United States Patent
Kita

(10) Patent No.: US 7,290,294 B2
(45) Date of Patent: Nov. 6, 2007

(54) PROTECTIVE GOGGLES

(75) Inventor: Tadashi Kita, Higashiosaka (JP)

(73) Assignee: Yamamoto Kogaku Co., Ltd., Osaka (JP)

( * ) Notice: Subject to any disclaimer, the term of this patent is extended or adjusted under 35 U.S.C. 154(b) by 77 days.

(21) Appl. No.: 10/661,743

(22) Filed: Sep. 12, 2003

(65) Prior Publication Data

US 2004/0088779 A1    May 13, 2004

(30) Foreign Application Priority Data

Sep. 13, 2002    (JP)    ............... 2002-268351

(51) Int. Cl.
   *A61F 9/02*    (2006.01)
(52) U.S. Cl. ....................................... 2/443
(58) Field of Classification Search ............ 2/439–441, 2/443, 428, 430; 351/43, 90, 92
   See application file for complete search history.

(56) References Cited

U.S. PATENT DOCUMENTS 5,862,621 A  *  1/1999  Karppanen ............... 43/17
5,950,248 A  *  9/1999  Kawashima et al. ........... 2/441
6,446,272 B1 *  9/2002  Lee ............................ 2/428
6,467,098 B1 * 10/2002  Lee ............................ 2/443

FOREIGN PATENT DOCUMENTS

| CN | 2072232 U | 2/1991 |
|---|---|---|
| JP | 52-36890 | 8/1977 |
| JP | 3-228763 | 10/1991 |
| JP | 3-231658 | 10/1991 |
| JP | 7-28577 | 5/1995 |

* cited by examiner

*Primary Examiner*—Katherine Moran
(74) *Attorney, Agent, or Firm*—Koda & Androlia

(57) ABSTRACT

A user may easily replace lenses in the protective goggles. The frame body is compositely made with a rigid frame member and a resilient frame member. An outer circumferential area of a replaceable lens abuts against the resilient frame member and also engages with the rigid frame member so as to be fixed together. The resilient frame member guarantees fluid-tightness (water-tightness or air-tightness) of the goggles and dispenses with a packing and the like.

24 Claims, 13 Drawing Sheets

PROTECTIVE GOGGLES

TECHNICAL FIELD OF THE INVENTION

The present invention relates to protective goggles to be used for dust protective goggles, swimming goggles or the like.

DESCRIPTION OF THE PRIOR ART

There have been protective goggles that protect users' eyes, such as swimming goggles.

There are occasional demands for modifying such swimming goggles, for example, by changing lenses to dioptrical lenses or polarized lenses suitable for a user's eyesight, to colored lenses for a user's preference, or darker or lighter lenses according to surrounding brightness.

For the foregoing purposes, some types of goggles have lenses that are replaceable by a user with respect to goggle frames (some are hard-type frames, others are soft-type frames that are relatively soft in material).

In case of the soft-type frame (e.g. shown in Japanese Utility Model Publication No. 61-154925, page 4, FIG. 1), the frame is liable to deform to cause a gap between a lens and the frame, and resulting in invasion of water. On the other hand, in case of the hard-type frame shown in FIG. 13 (e.g. shown in Japanese Utility Model Publication No. 60-25645, page 8, FIG. 10), a packing 23 (e.g., made of silicon rubber) is provided between a frame 21 and a lens 22 in order to obtain water-tightness, however, when inserting a replaceable lens into the frame 21, the packing 23 is prone to be out of position and replacement of lenses is not easy.

SUMMARY OF THE INVENTION

It is, therefore, an object of the present invention to provide protective goggles in which lenses may be replaced by a user easier than in conventional goggles.

In order to achieve the above object, the present invention has the following advantageous features.

(1) In the protective goggles in the present invention, a frame body is compositely formed with a rigid frame member and a resilient frame member. The combination of the rigid and the resilient frame member. or the frame body, receives a replaceable lens at its front face side. An outer circumferential area of the replaceable lens abuts against the resilient frame member and also engages with the rigid frame member so that the lens and the frame members are fixed together.

Since the frame being a combination of the rigid and the resilient frame member receives the replaceable lens at its front face side, the lens may readily be replaced in the state where the frame members are combined.

Since the outer circumferential area of the replaceable lens abuts against the resilient frame member, fluid-tightness (water-tightness and air-tightness) between the lens and the frame body can be guaranteed by the resilient member, and thereby resulting in dispensing with a packing or the like.

The outer circumferential area of the lens is also fixed by an engagement with the rigid frame member, and the rigid frame member guarantees resistance to deformability of the whole frame body in use. Therefore, water invasion during use (swimming) through a gap due to deformation of the frame body may be prevented.

The lens and the frame members do not have to be in an exact fixation position, but may be more or less off from it as long as they cause no trouble in use. The outer circumferential area of the lens may be engaged indirectly with the rigid frame member through the resilient frame member. For example, the rigid frame member is sandwiched or surrounded by the resilient frame member.

(2) The outer circumferential area of the lens may have a flange portion and a stopping portion. With this structure, the thickness of the rigid and resilient frame members may be absorbed by the flange portion and the two frame members may be fixed with the stopping portion.

(3) The flange portion and the stopping portion may be provided at least one portion of an outer circumference of the lens. Namely, they may extend only a certain circumferential length or may be extend around the whole outer circumference.

Although the flange portion and the stopping portion may extend only a part of the outer circumference of the lens, when they extend around the whole outer circumference of the lens, the lens is reliably fixed on the frame body even when power is applied in use and the strength against deformation becomes sufficient, and the protective goggles excellent in strength may be obtained.

(4) The stopping portion of the outer circumferential area of the lens may be engaged and fixed with the rigid frame member.

With this structure, the stopping portion and the rigid frame member, both made of hard material, are engaged with each other and fixed together. As a result, strength and durability in the protective goggles become superior.

(5) The lens may be stretched to provide a tab portion. With this structure, at the time of attaching and detaching of lenses, a user may manipulate the lens holding the tab portion so that a user's finger print may be prevented from being left on the lens face.

(6) A face-abutting cushion member may be formed in one body with and by the resilient frame member. Then the frame member with the face-abutting cushion member may be readily, advantageously formed.

(7) A nose bridge member which connects a left frame side and a right frame side may be formed in one body with and by the resilient frame member. With this structure, the resilient frame member with the nose bridge member may be readily produced.

DETAILED DESCRIPTION OF THE INVENTION

Embodiments of protective goggles of the present invention are described below in conjunction with the accompanying drawings. In the respective embodiments, protective goggles are provided in the form of swimming goggles.

EMBODIMENT 1

Figure 1:
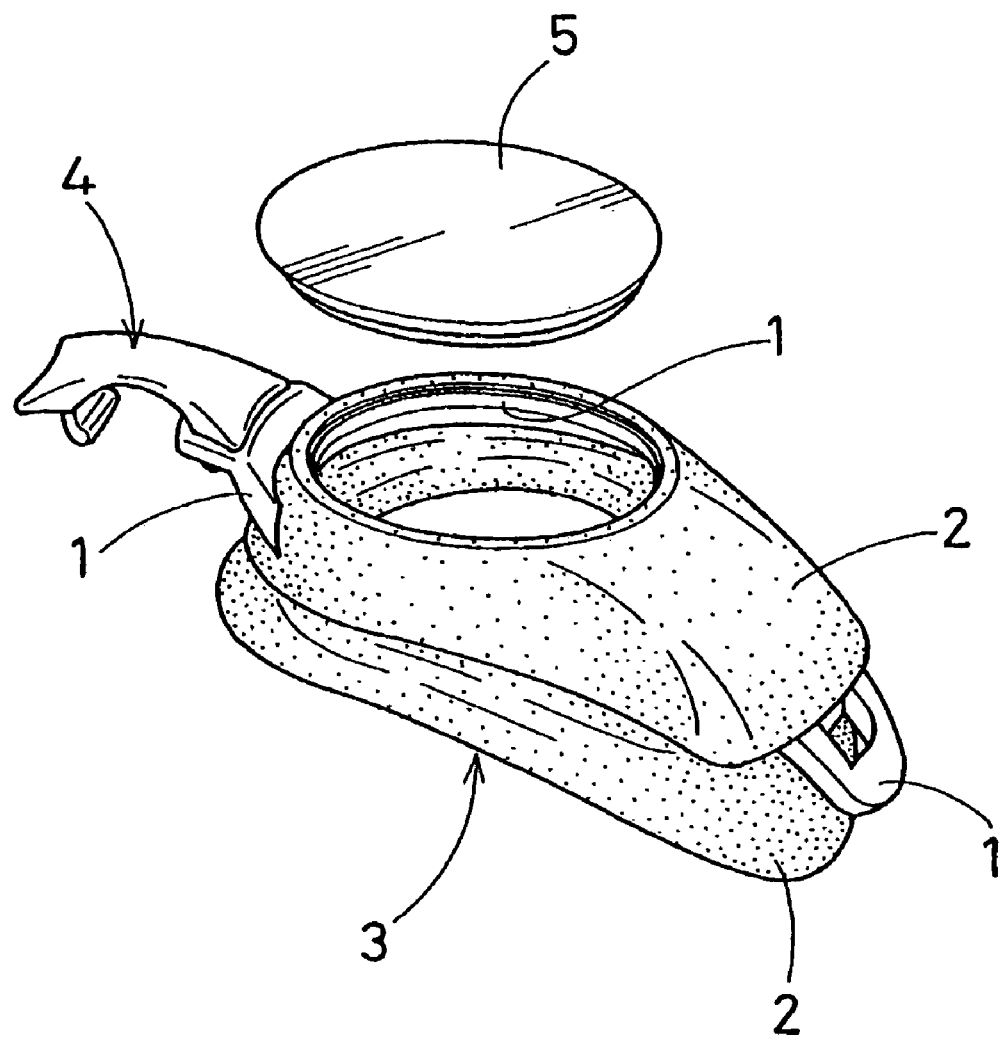
FIG. 1 is an exploded perspective view showing main parts of Embodiment 1 of protective goggles (swimming goggles) according to the present invention.
Figure 2:
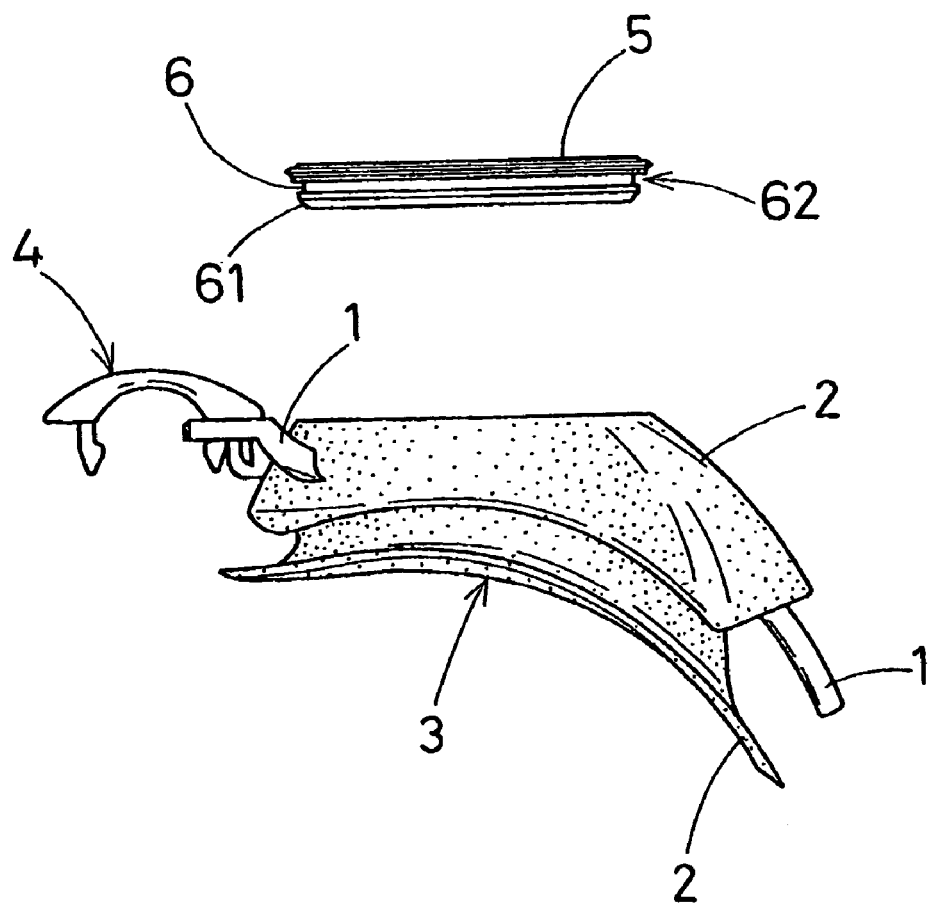
FIG. 2 is a side view of the protective goggles in FIG. 1.
Figure 3:
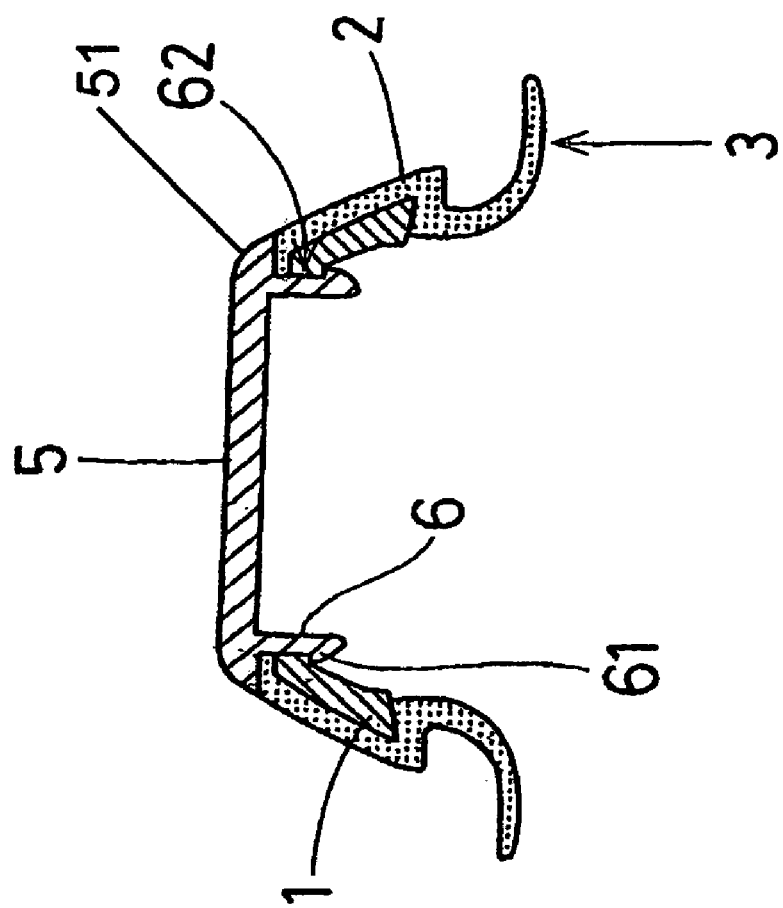
FIG. 3 is a sectional view of main parts exaggeratedly drawn to explain the sectional structure of the protective goggles in FIG. 1.

Referring to FIGS. 1 to 3, swimming goggles of this embodiment includes a frame body compositely having a rigid frame member 1 and a resilient frame member 2 which is relatively softer than the rigid frame member 1. Numeral 3 denotes a face-abutting cushion member, made in one body with and by the resilient frame member 2. Numeral 4 denotes a nose bridge member connecting left and right frames together. A replaceable lens 5 is received detachably with and from the frame body at its front face side. More specifically the lens 5 is replaceable by being attached with and detached from the front face side of the frame body which is the combination of the rigid frame member 1 and the resilient frame member 2.

Materials of the rigid frame member 1 are plastic such as polycarbonate and polypropylene. Materials of the resilient frame member 2 include, for example, silicon rubber and thermoplastic elastomer resin which has resiliency and flexibility. The rigid and the resilient frame members 1 and 2 may be integrated (bonded together) by insert forming (molding) or two-color forming.

As seen in FIGS. 2 and 3, an outer circumferential area of the lens 5 extends to form a flange portion 6 and a stopping portion 61. A stepped groove 62 is defined by the area surrounded by a lens 5, the flange portion 6 and the stopping portion 61. Also, a circumferential flange 51 is provided surrounding the front surface of lens 5 and engages with the front face side of the frame body.

The outer circumferential area of the lens 5, which is replaceable, not only abuts against the resilient frame member 2 but also meshes with the rigid frame member 1, so that the lens 5 is fixed with the frame body. More specifically, the stopping portion 61 of the outer circumferential area of the lens 5 fixedly engages with the rigid frame member 1. Here, hard two elements, i.e. the stopping portion 61 and the rigid frame member 1, are engaged with each other and fixed together, and this enhances strength and durability.

The flange portion 6 and the stopping portion 61 extend around the whole outer circumference of the lens 5. Thus even force is applied during swimming, the lens 5 is reliably fixed with the frame body and the frame body is free from deformation, and thereby resulting in providing excellent strength. It is sufficient that the flange portion 6 and the stopping portion 61 extend at least a portion of the outer circumferential area.

The swimming goggles of this embodiment may be used as follows.

In the swimming goggles, the replaceable lens may be readily replaced by removing it from or attaching it to the front face side of the frame body which is the combination of the rigid and resilient frame members 1 and 2. The outer circumferential area of the replaceable lens 5 abuts against the resilient frame member 2, and the resilient frame member 1 guarantees water-tightness around the outer circumferential area of the lens 5. This structure requires no packing member therearound, and further facilitates easier change of lens 5 than conventional goggles. In other words, high quality goggles with replaceable or spare lenses 5 may become available.

The outer circumferential area of the lens 5 is also fixedly engaged with the rigid frame member 1. This rigid frame member 1 guarantees resistance to deformation of the frame body as a whole in use. Water invasion during swimming through a gap caused by the deformation of the goggles will be eliminated.

The face-abutting cushion member 3 is formed as one body with and by the resilient frame member 2, and the resilient frame member 2 including the face-abutting cushion member 3 is fabricated readily and favorably.

The protective goggles may be used for dust preventive purposes with air-tightness, instead of water-tightness. Protective goggles may be prepared as two-glass type like this embodiment as well as single-glass type (not shown).

EMBODIMENT 2

Embodiment 2 is described below highlighting differences from Embodiment 1.

As shown in FIGS. 4 to 8, in the swimming goggles of this embodiment, the frame body compositely includes a rigid frame member 1 and a resilient frame member 2 which is relatively soft in material. Numeral 7 denotes a resilient belt with which the goggles are held on a user's head.

Figure 4:
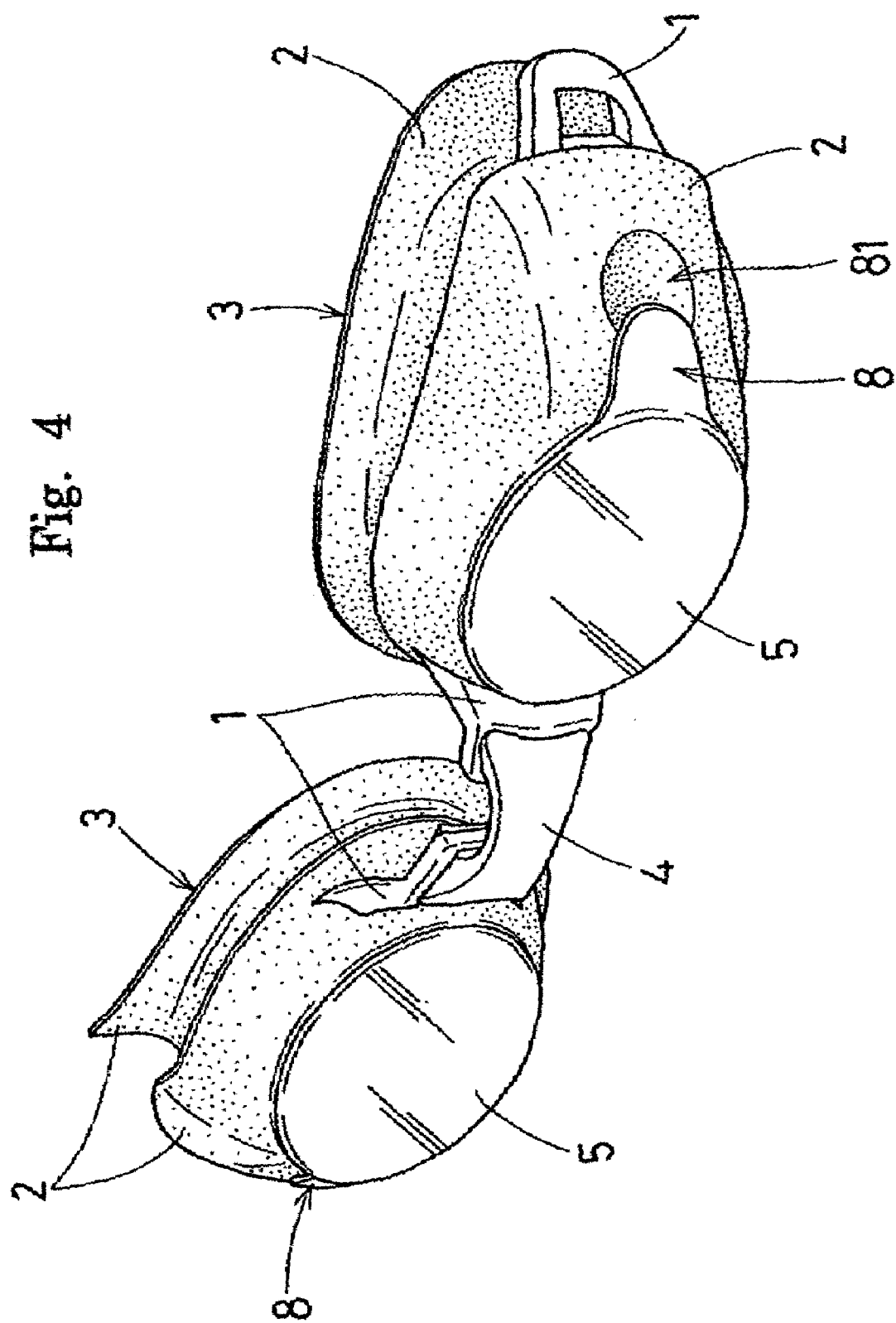
FIG. 4 is an overall perspective view showing Embodiment 2 of protective goggles (swimming goggles) according to the present invention.
Figure 5:
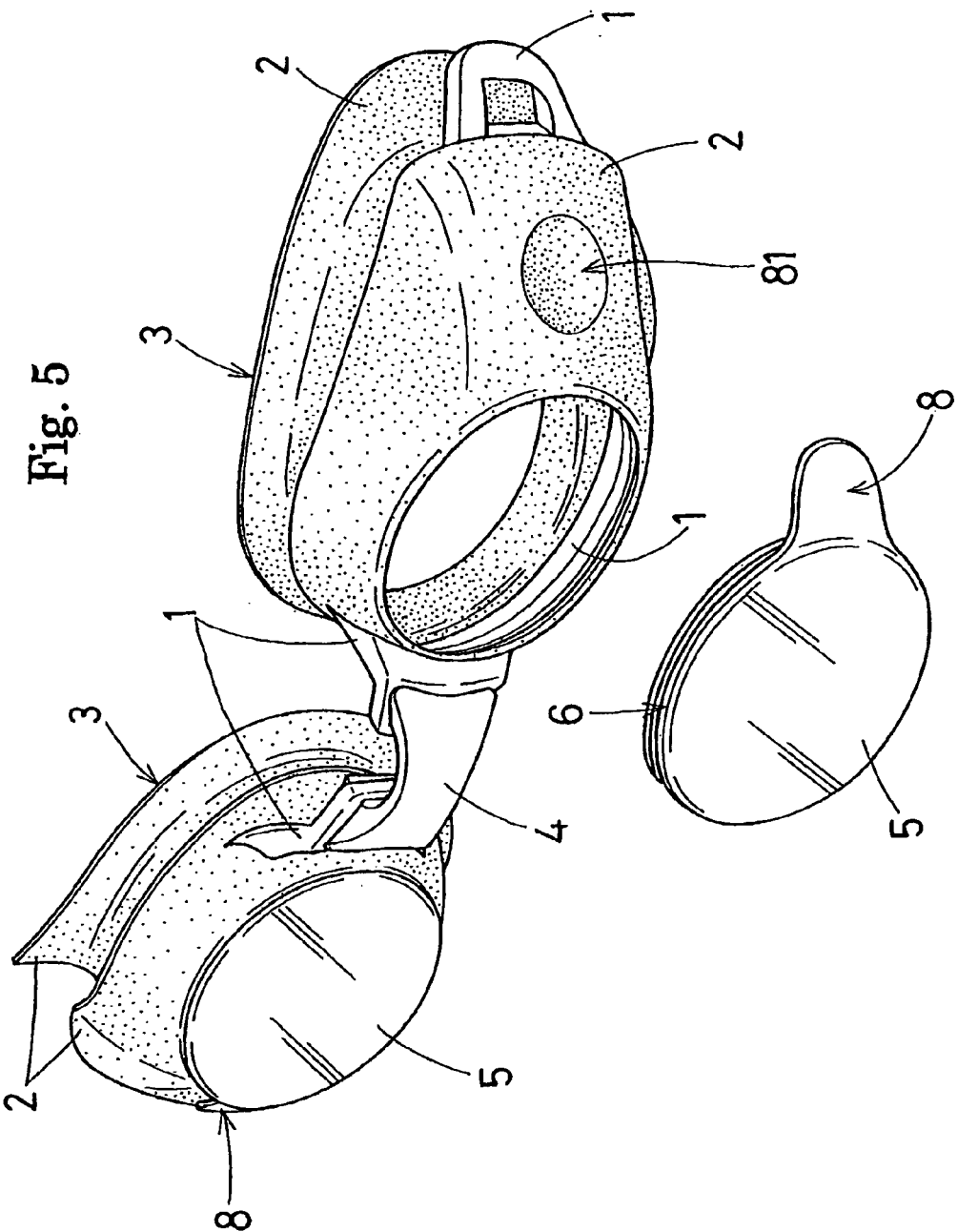
FIG. 5 is a partially exploded perspective view of the protective goggles in FIG. 4.
Figure 7:
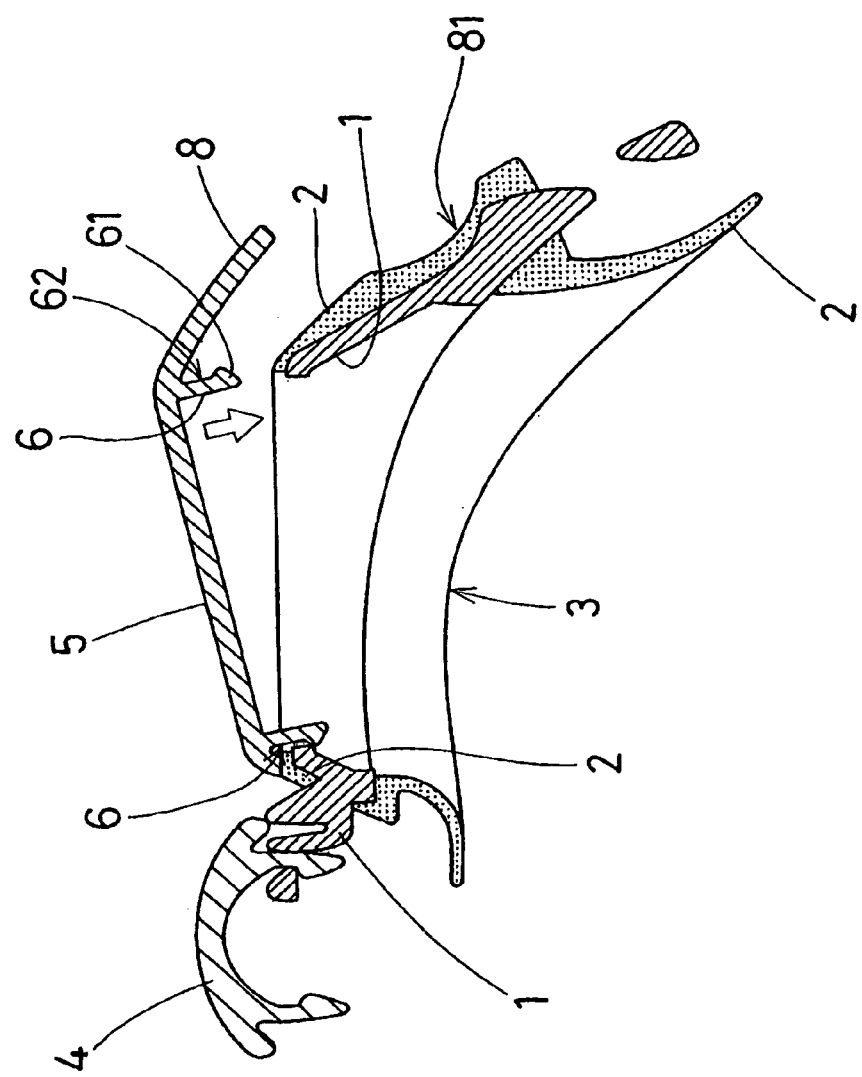
FIG. 7 is an enlarged sectional view of main parts in the protective goggles in FIG. 4 in which a replaceable lens is being engaged with a frame body.

As shown in FIGS. 4 and 5, each of lenses has a tab portion 8 as a manipulating piece for replacement; more specifically a left lens has a tab portion stretching from its left side and a right lens has a tab portion stretching from its right side. At the time of attaching and detaching of lenses, a user can do so holding the tab portion 8 so as to extremely prevent the lens surface 5 per se from getting dirty with fingerprints or the like. A dent 81 is provided at a portion of the resilient frame member 2 corresponding to the position of the tab portion 8. With this structure, a user can insert easily his or her thumb or fingers between the tab portion 8 and the resilient frame member 2, which facilitates easy removal or attachment of the lens 5. FIG. 7 shows the state where the replaceable lens 5 is being pushed to the front face side of the frame body (the combination of the rigid and resilient frame members 1 and 2) into an engagement.

Figure 6:
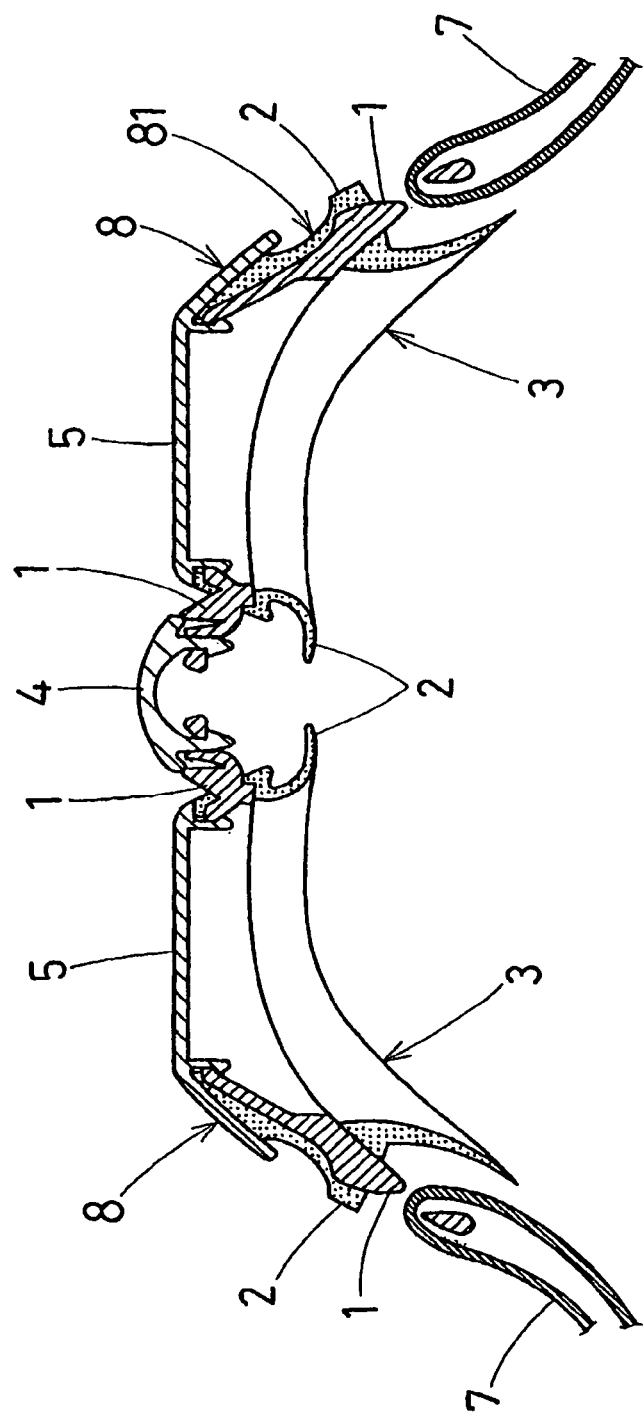
FIG. 6 is a sectional view of the protective goggles in FIG. 4.
Figure 8:
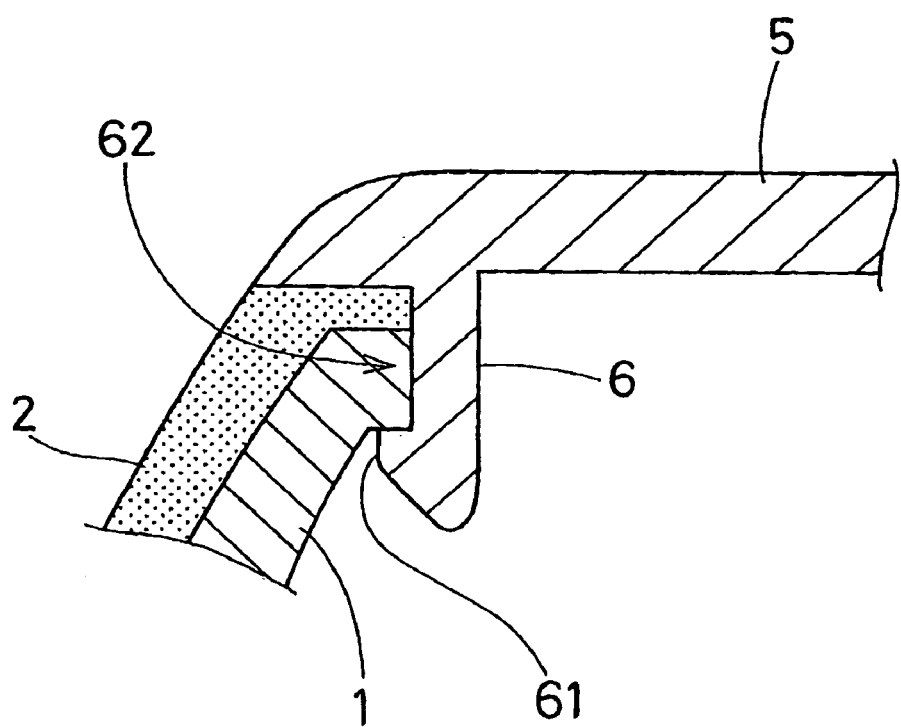
FIG. 8 is an enlarged view of main parts of the protective goggles in FIG. 6.

Also as shown in FIGS. 6 to 8, the whole outer circumference of the replaceable lens 5 not only abuts against the resilient frame member 2 at the front side but also engages (meshes) with the rigid frame member 1 at the rear side, thereby the three members are fixed together.

Next, the state of the swimming goggles of this embodiment in use is described.

As shown in FIGS. 6 to 8, in the swimming goggles, the replaceable lens may be readily replaced by removing it from and attaching it to the front face side of the frame body being the combination of the rigid and resilient frame members 1 and 2. The outer circumferential area of the replaceable lens 5 not only abuts against the resilient frame member 2 at the front side but also engages with the rigid frame member 1 at the rear side so as to be fixed together. The outer circumferential area of the lens 5 that abuts against the resilient frame member 2 also engages (meshes) with the rigid frame member 1 so as to be fixed together and a sealing effect or water-tightness is obtained.

Also abutment of the outer circumferential area of the lens 5 against the resilient frame member 2 necessitates no existence of a packing. Therefore, this advantageously enables easier replacement of lens 5 for a user than conventional goggles.

Figure 9:
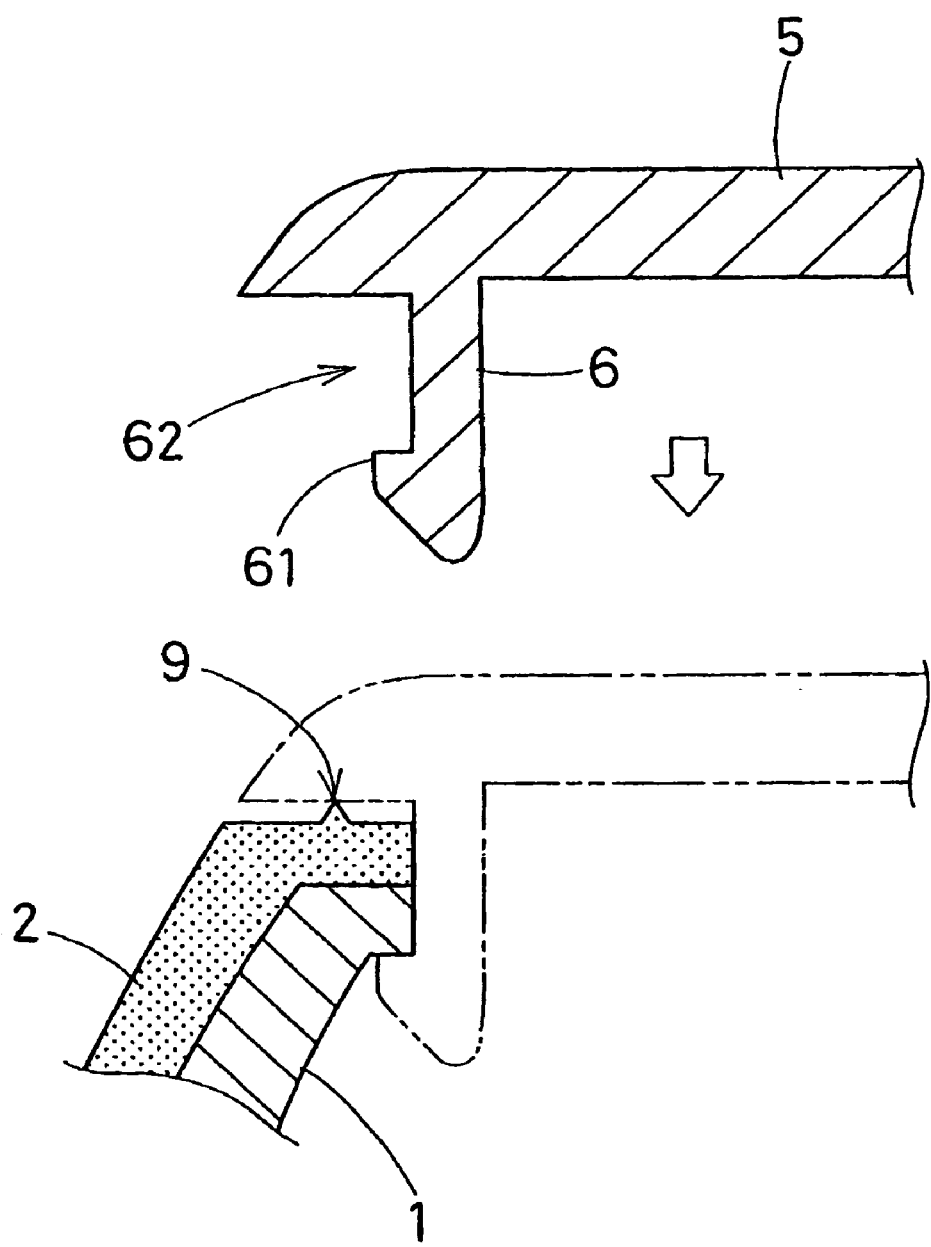
FIG. 9 is an enlarged view of main parts of another embodiment of the protective goggles in FIG. 8.
Figure 10:
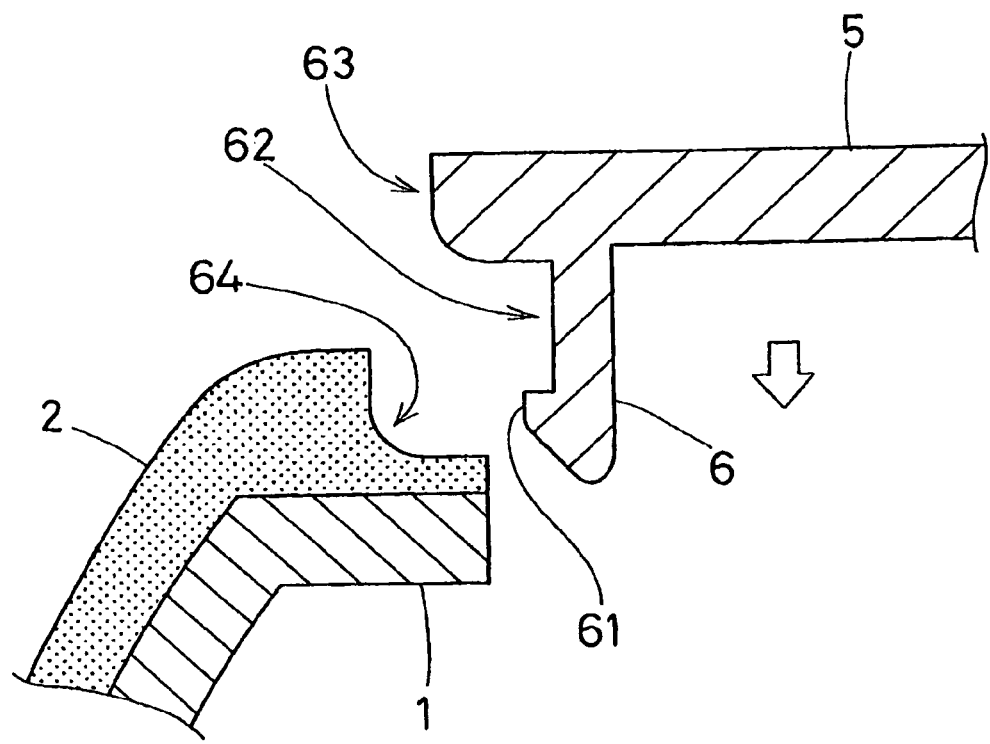
FIG. 10 is an enlarged view of main parts of another embodiment of the protective goggles in FIG. 8.
Figure 11:
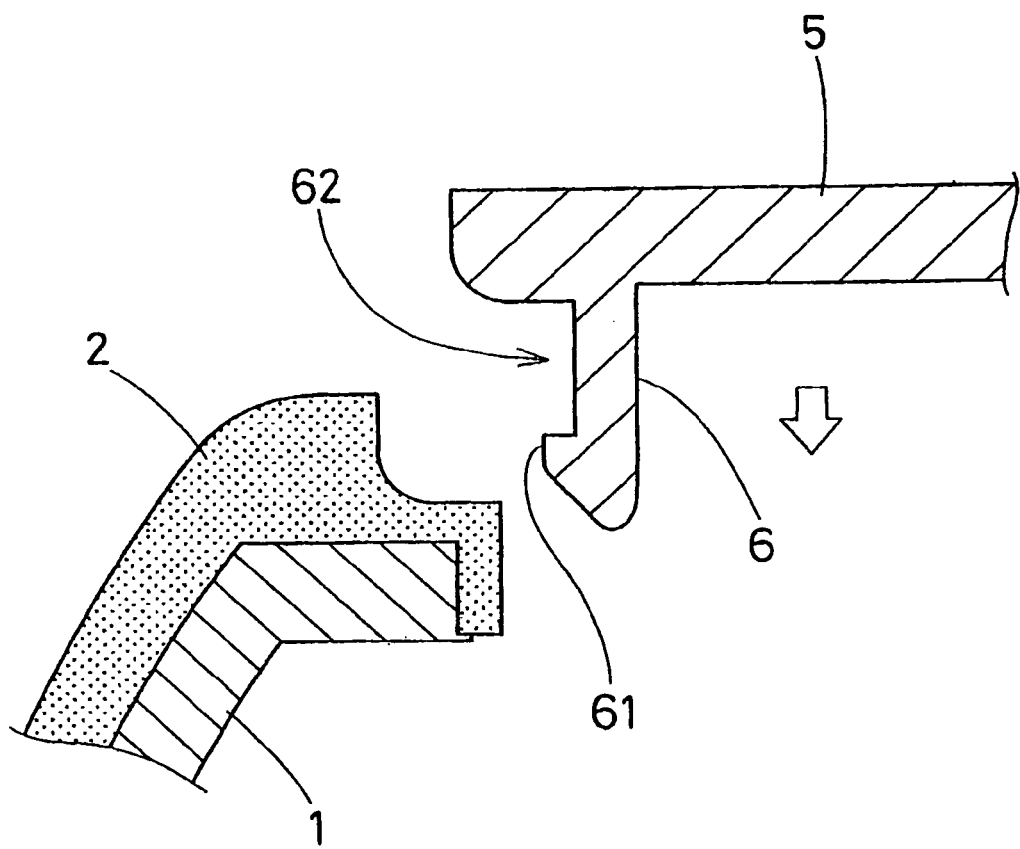
FIG. 11 is an enlarged view of main parts of another embodiment of the protective goggles in FIG. 8.

Joining area among the outer circumferential area of the lens 5, the resilient frame member 2 and the rigid frame member 1 in this embodiment is constituted as shown in FIG. 8, but not limited thereto. The joining area may optionally be made in a manner that an annular projection 9 is provided on the resilient frame member 2 to enhance the water-tightness with the lens 5 as shown in FIG. 9, or that an outer ridge area 63 of the lens 5 is protected by an cutout 64 of the resilient frame member 2 and front sides of the lens 5 and the resilient frame member 2 are flush to obtain sharp and neat impression in its design and appearance. Furthermore, as shown in FIG. 11, the front side of the resilient frame member 2 is extended to an end portion of the rigid frame member 1 so as to improve the water-tightness with regard to the lens 5.

EMBODIMENT 3

Embodiment 3 is described below focusing on difference from the foregoing embodiments.

Figure 12:
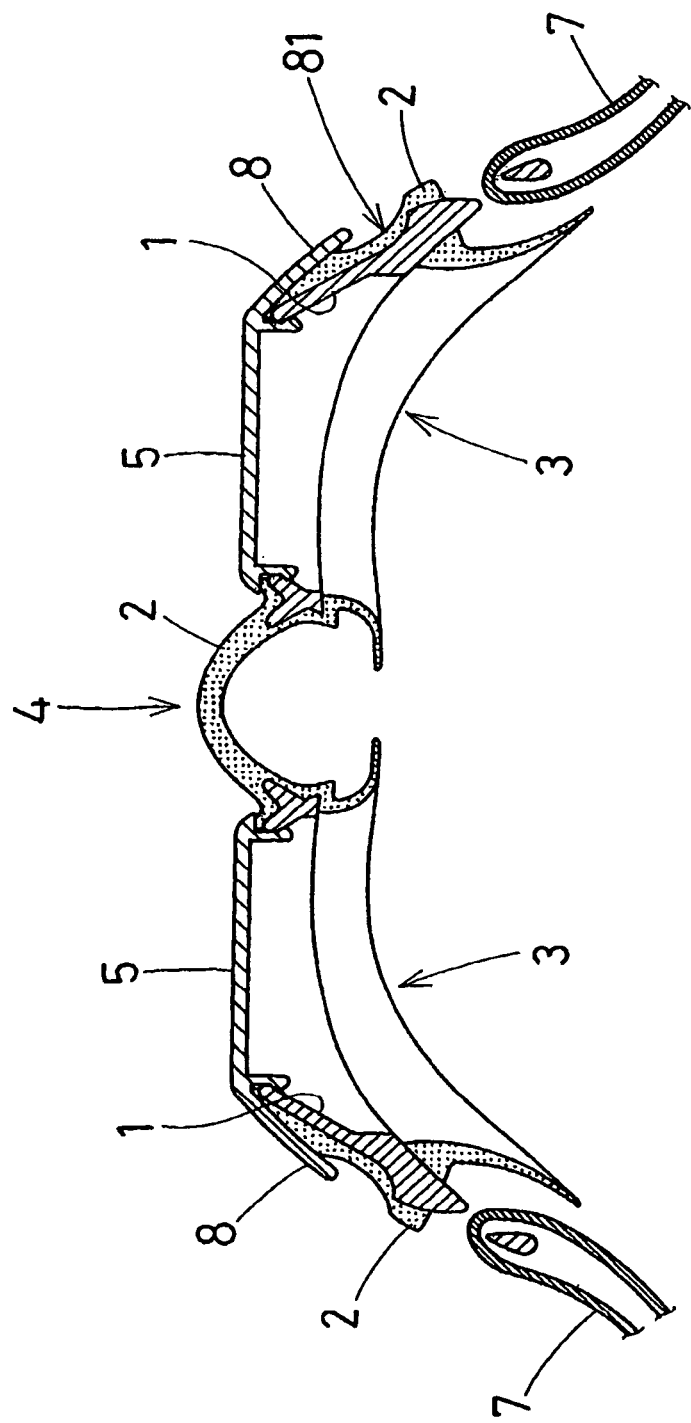
FIG. 12 is a sectional view showing Embodiment 3 of protective goggles (swimming goggles) according to the present invention.
Figure 13:
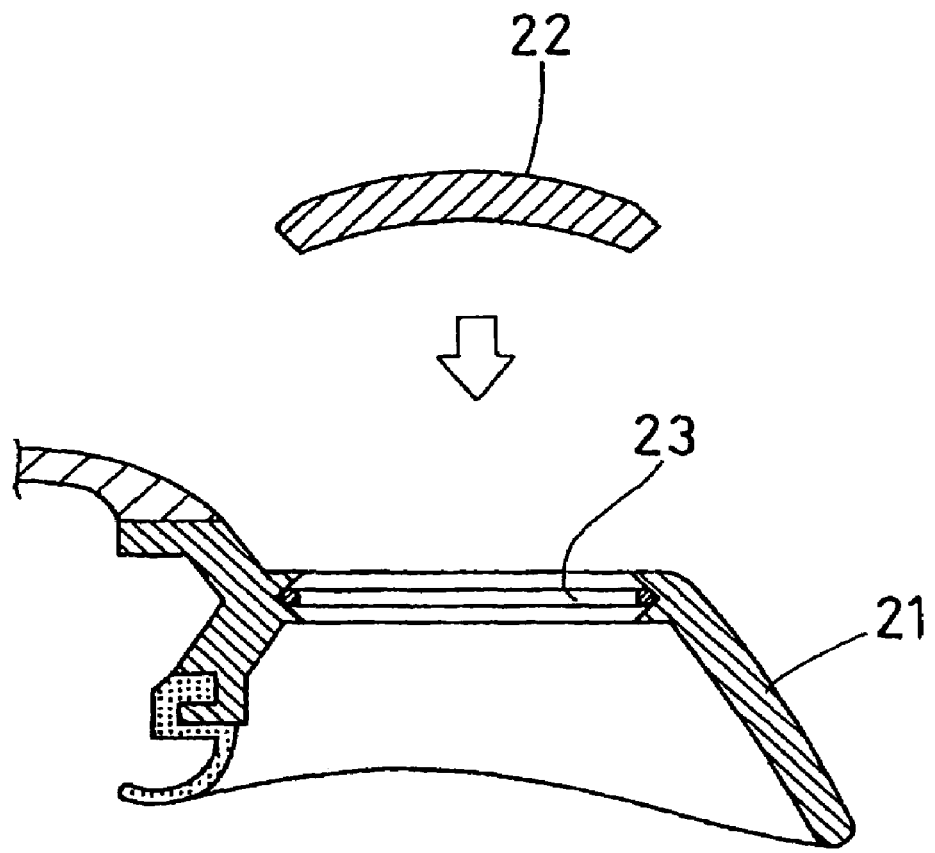
FIG. 13 is an enlarged sectional view of main parts showing conventional protective goggles.

Referring to FIG. 12, a nose bridge member 4 connecting the right and the left frames is formed in one body with and by the resilient frame member 2. Forming of the resilient frame member 2 including the nose bridge member 4 may be readily and favorably done.

With the structure stated above, in the protective goggles of the present invention, the replaceable lens 5 may readily be attached with and detached from the front face side of the frame body in which the rigid and resilient frame members 1 and 2 are combined. The outer circumferential area of the lens not only abuts against the resilient frame member but also engages with the rigid frame so that the lens is fixed together with the frame members and fluid-tightness may be obtained. Furthermore, abutment of the outer circumferential area of the lens against the resilient frame member necessitates no existence of a packing or the like. As a result the goggles in which the lens may be more readily and reliably replaced by a user compared with conventional goggles is provided.

What is claimed is:
1. Protective goggles comprising:
   a frame body compositely formed with a rigid frame member and a resilient frame member, said resilient frame member having a face abutting cushion member;
   at least one replaceable lens having an outer circumferential area;
   a circumferential flange provided on said outer circumferential area surrounding a front surface of said replaceable lens such that said circumferential flange abuts against a front face side of said frame body and the lens alone is detachable with and from said front face side of the frame body, said front face side being on a side of said frame body opposite said face abutting cushion member; and
   wherein the outer circumferential area of said replaceable lens abuts against the resilient frame member and engages with the rigid frame member.
2. The protective goggles according to claim 1, wherein the outer circumferential area of the replaceable lens is provided with a flange portion and a stopping portion and the stopping portion is engaged with the rigid frame member to be fixed together.
3. The protective goggles according to claim 2, wherein the flange portion and the stopping portion are provided on at least a portion of a whole circumference of the lens.
4. The protective goggles according to claim 3, wherein the lens is extended to provide a tab portion thereto for facilitating removal and insertion of said replaceable lens.
5. The protective goggles according to claim 4, wherein a face-abutting cushion member is formed in one body with and by the resilient frame member.
6. The protective goggles according to claim 5, wherein a nose bridge member connecting a right side and a left side of the frame body together is formed in one body with and by the resilient frame member.
7. The protective goggles according to claim 4, wherein a nose bridge member connecting a right side and a left side of the frame body together is formed in one body with and by the resilient frame member.
8. The protective goggles according to claim 3, wherein a face-abutting cushion member is formed in one body with and by the resilient frame member.
9. The protective goggles according to claim 8, wherein a nose bridge member connecting a right side and a left side of the frame body together is formed in one body with and by the resilient frame member.
10. The protective goggles according to claim 3, wherein a nose bridge member connecting a right side and a left side of the frame body together is formed in one body with and by the resilient frame member.
11. The protective goggles according to claim 2, wherein the lens is extended to provide a tab portion thereto for facilitating removal and insertion of said replaceable lens.
12. The protective goggles according to claim 11, wherein a face-abutting cushion member is formed in one body with and by the resilient frame member.
13. The protective goggles according to claim 12, wherein a nose bridge member connecting a right side and a left side of the frame body together is formed in one body with and by the resilient frame member.
14. The protective goggles according to claim 11, wherein a nose bridge member connecting a right side and a left side of the frame body together is formed in one body with and by the resilient frame member.
15. The protective goggles according to claim 2, wherein a face-abutting cushion member is formed in one body with and by the resilient frame member.
16. The protective goggles according to claim 15, wherein a nose bridge member connecting a right side and a left side of the frame body together is formed in one body with and by the resilient frame member.
17. The protective goggles according to claim 2, wherein a nose bridge member connecting a right side and a left side of the frame body together is formed in one body with and by the resilient frame member.
18. The protective goggles according to claim 1, wherein the lens is extended to provide a tab portion thereto for facilitating removal or insertion of said replaceable lens.
19. The protective goggles according to claim 18, wherein a face-abutting cushion member is formed in one body with and by the resilient frame member.

20. The protective goggles according to claim 19, wherein a nose bridge member connecting a right side and a left side of the frame body together is formed in one body with and by the resilient frame member.

21. The protective goggles according to claim 18, wherein a nose bridge member connecting a right side and a left side of the frame body together is formed in one body with and by the resilient frame member.

22. The protective goggles according to claim 1, wherein a face-abutting cushion member is formed in one body with and by the resilient frame member.

23. The protective goggles according to claim 22, wherein a nose bridge member connecting a right side and a left side of the frame body together is formed in one body with and by the resilient frame member.

24. The protective goggles according to claim 1, wherein a nose bridge member connecting a right side and a left side of the frame body together is formed in one body with and by the resilient frame member.

* * * * *